(12) United States Patent
Welck

(10) Patent No.: US 9,943,745 B2
(45) Date of Patent: Apr. 17, 2018

(54) DIGITAL VIDEO RAMP

(71) Applicant: Steve Welck, Lahaina, HI (US)

(72) Inventor: Steve Welck, Lahaina, HI (US)

(73) Assignee: Steve Weick, Costa Mesa, CA (US)

( * ) Notice: Subject to any disclaimer, the term of this patent is extended or adjusted under 35 U.S.C. 154(b) by 0 days.

(21) Appl. No.: 15/003,799

(22) Filed: Jan. 21, 2016

(65) Prior Publication Data

US 2016/0210104 A1  Jul. 21, 2016

Related U.S. Application Data

(60) Provisional application No. 62/106,210, filed on Jan. 21, 2015.

(51) Int. Cl.

| | | |
|---|---|---|
| *A63G 19/10* | (2006.01) | |
| *A63B 71/06* | (2006.01) | |
| *G09F 9/302* | (2006.01) | |
| *G09F 9/30* | (2006.01) | |
| *G09F 19/22* | (2006.01) | |
| *A61B 5/11* | (2006.01) | |
| *A63C 19/00* | (2006.01) | |
| *E01C 13/00* | (2006.01) | |
| *G06F 3/01* | (2006.01) | |
| *G06T 19/00* | (2011.01) | |
| *G06T 19/20* | (2011.01) | |
| *G06F 3/00* | (2006.01) | |
| *A63B 69/00* | (2006.01) | |
| *G02F 1/1333* | (2006.01) | |

(52) U.S. Cl.
CPC ........... *A63B 71/0619* (2013.01); *A61B 5/11* (2013.01); *A63C 19/00* (2013.01); *E01C 13/003* (2013.01); *G06F 3/011* (2013.01); *G06T 19/006* (2013.01); *G06T 19/20* (2013.01); *G09F 9/301* (2013.01); *G09F 9/3026* (2013.01); *G09F 19/22* (2013.01); *A63B 69/0022* (2013.01); *A63B 2071/0658* (2013.01); *G02F 1/13336* (2013.01); *G06T 2207/30221* (2013.01)

(58) Field of Classification Search
CPC ........ A63G 19/00; A63G 19/10; A63G 31/00; A63G 31/16; G06F 3/00; G06F 3/1446
USPC .......................... 472/88–91, 59–61; 345/1.3
See application file for complete search history.

(56) References Cited

U.S. PATENT DOCUMENTS

| | | | | |
|---|---|---|---|---|
| 5,482,510 A | * | 1/1996 | Ishii ...................... | A63G 31/16 472/61 |
| 5,961,195 A | * | 10/1999 | Yoshimatsu ........... | G09B 9/058 353/122 |
| 7,967,692 B2 | * | 6/2011 | Werner .................. | A63G 21/18 434/44 |
| 2014/0333507 A1 | * | 11/2014 | Welck .................. | G06F 3/1446 345/1.3 |

* cited by examiner

*Primary Examiner* — Kien Nguyen
(74) *Attorney, Agent, or Firm* — Wong & Rees LLP; Kirk D. Wong

(57) ABSTRACT

A digital video ramp assembly incorporates process-formed structural LED tiles with modular components that join in a system of scalable structural LED tiles forming a complete LED display structure with integrated LED embedded tiles with interlocking and inter-trans-positioning features sometimes requiring additional structural framing.

18 Claims, 22 Drawing Sheets

Video Ramp Assembly Type A - Section
Basic Ramp Construction and Shapes

LED Ramp Assembly Type A

Top View

Front View

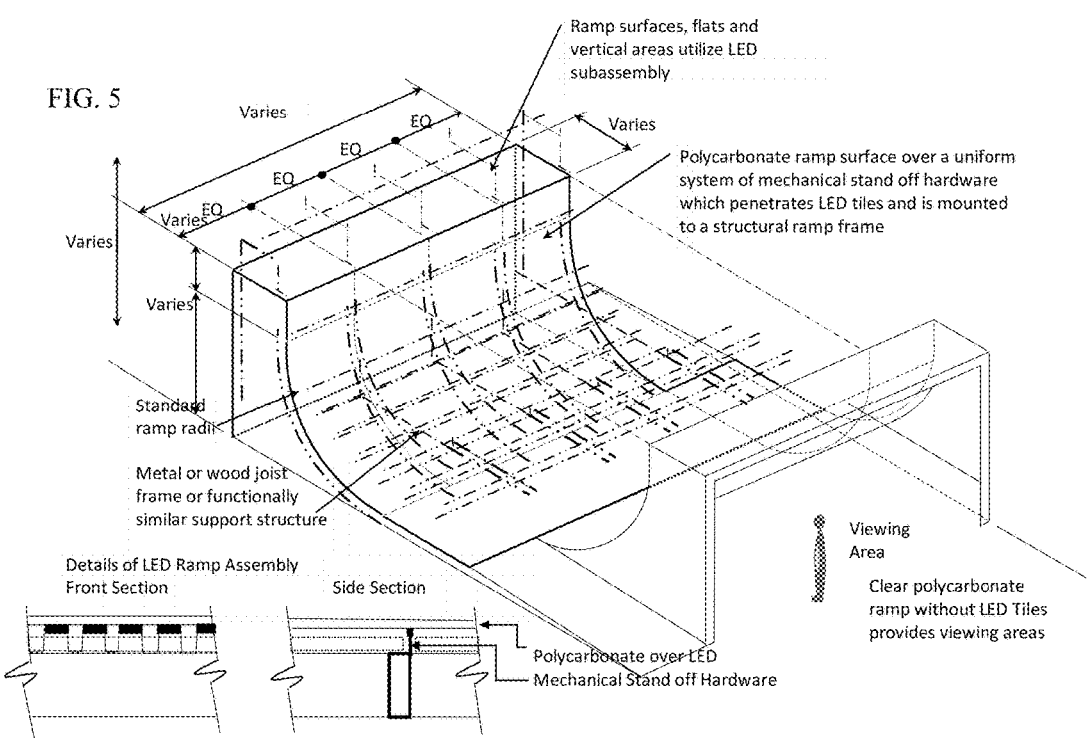

Structural LED ramp system, comprising: a plurality of LED tiles each forming a complete ramp surface with a durable surface or clear protective layer atop a sub frame layer comprising a matrix of intersecting structural members and fasteners adapted to fit within the outer boundary corners of each ramp form Side View

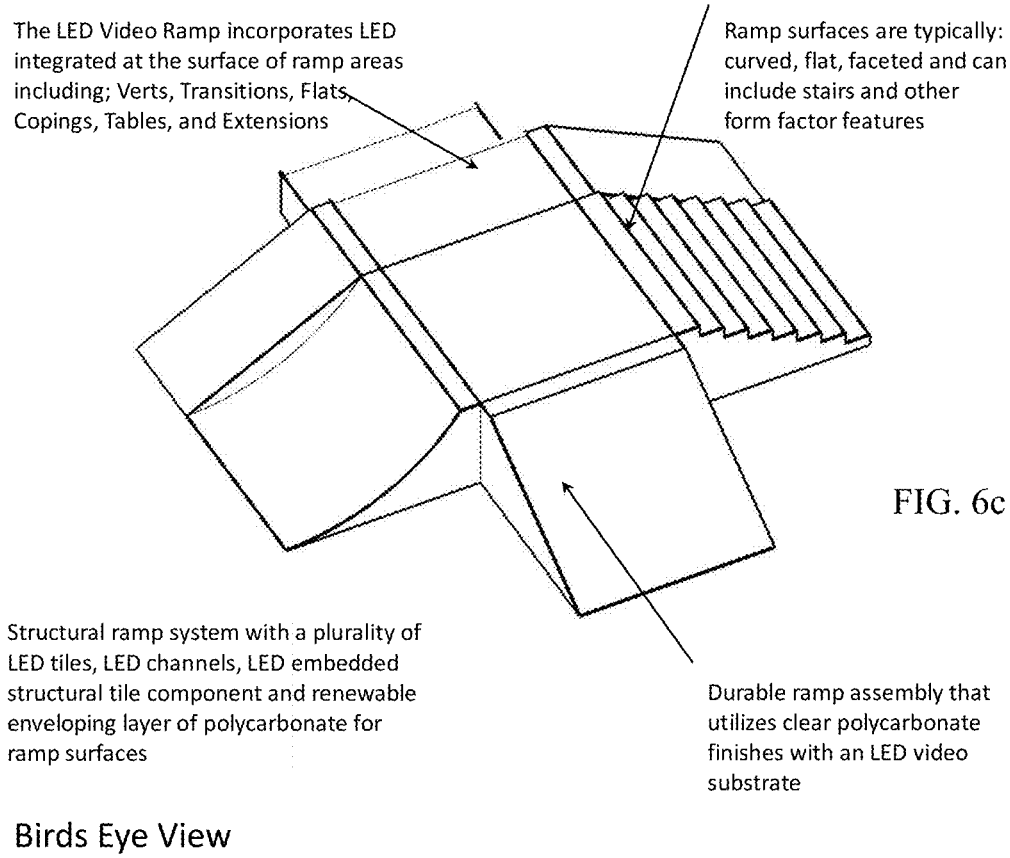

FIG. 6c

The LED Video Ramp incorporates LED integrated at the surface of ramp areas including; Verts, Transitions, Flats, Copings, Tables, and Extensions Ramp surfaces are typically: curved, flat, faceted and can include stairs and other form factor features Structural ramp system with a plurality of LED tiles, LED channels, LED embedded structural tile component and renewable enveloping layer of polycarbonate for ramp surfaces Durable ramp assembly that utilizes clear polycarbonate finishes with an LED video substrate Birds Eye View Plan View Side View

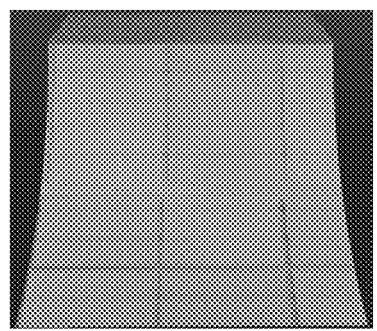 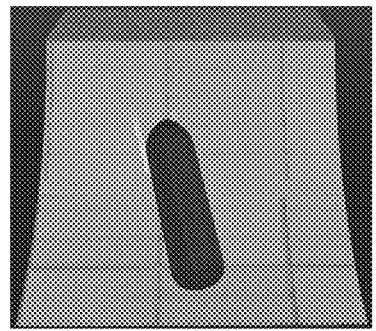
Ramp from point of view of overhead camera.
Overlaid video content corresponding with moving skate board
FIG. 9

DIGITAL VIDEO RAMP

PRIORITY CLAIM

This application claims benefit of Provisional Application No. 62/106,210, filed Jan. 21, 2015, the entire contents of which is hereby incorporated by reference as if fully set forth herein, under 35 U.S.C. § 119(e).

TECHNICAL FIELD

Embodiments relate generally to digital display systems, and, more specifically, to techniques for incorporating digital displays into ramps.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Ramp structures maybe used for many purposes. One of the more popular uses is in skating, such as a skating ramp. Other applications include motocross and bicycle motocross (BMX) competitions and exhibitions. Current ramp systems more often utilize a wood joist frame or functionally similar support structure and plywood or similar sheeting for side bracing. These ramps also incorporate standardized radii and surface materials. Ramps at skate parks often are constructed of wood or formed in concrete. Some exhibition ramps may have images projected onto the ramp using overhead projectors. The images are typically static logos or videos that are limited in size due to distortions caused by the contours of the ramp.

One of the major challenges with projection systems is that the image projected onto the ramp becomes distorted, out of focus, or out of proportion, due to the varying contours of the ramp. This is because the distance between the lens of the projector and the ramp surface cannot be consistent when the ramp incorporates any surface features such as simple or complex contours. Further, the dimensions of the ramp surface vary with each ramp and are not consistent with any standard projector viewing area. To compensate for the sizing inconsistencies, projectors are typically limited in their projection area and the resulting images are smaller than the actual ramp surface area.

BRIEF DESCRIPTION OF THE DRAWINGS

The present invention is illustrated by way of example, and not by way of limitation, in the figures of the accompanying drawings and in which like reference numerals refer to similar elements and in which:

FIG. 5 illustrates a half pipe digital video ramp assembly, according to an embodiment;

FIGS. 6a-6c illustrate a complex contour digital video ramp assembly, according to an embodiment;

FIG. 9 illustrates a motion detection system for a digital video ramp assembly, according to an embodiment.

DETAILED DESCRIPTION

Figure 1:
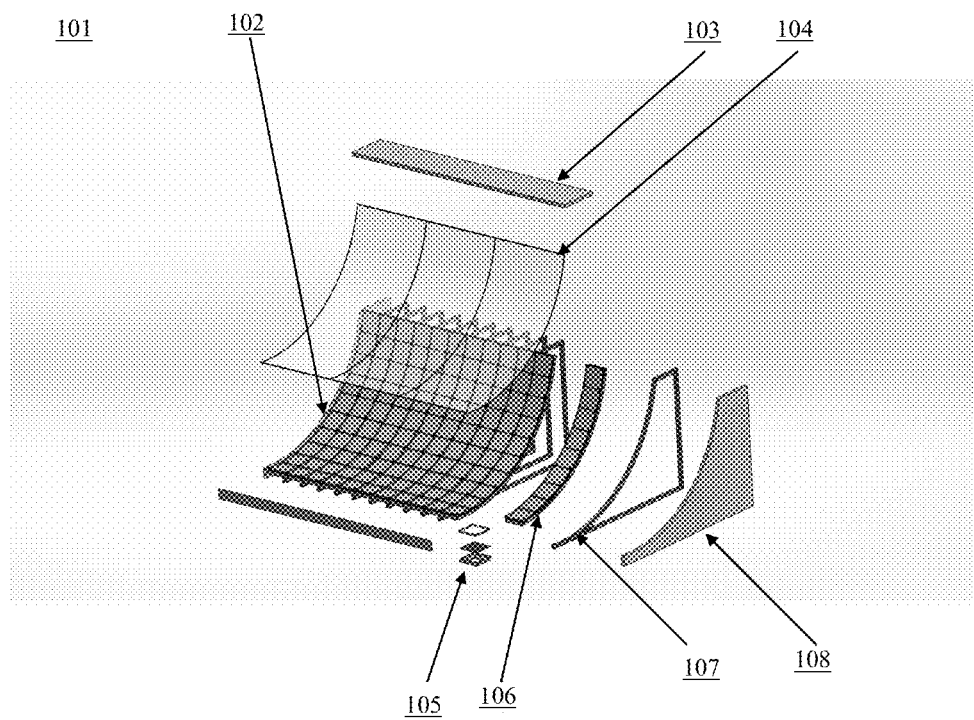
FIG. 1 illustrates a digital video ramp, according to an embodiment.
Figure 2A:
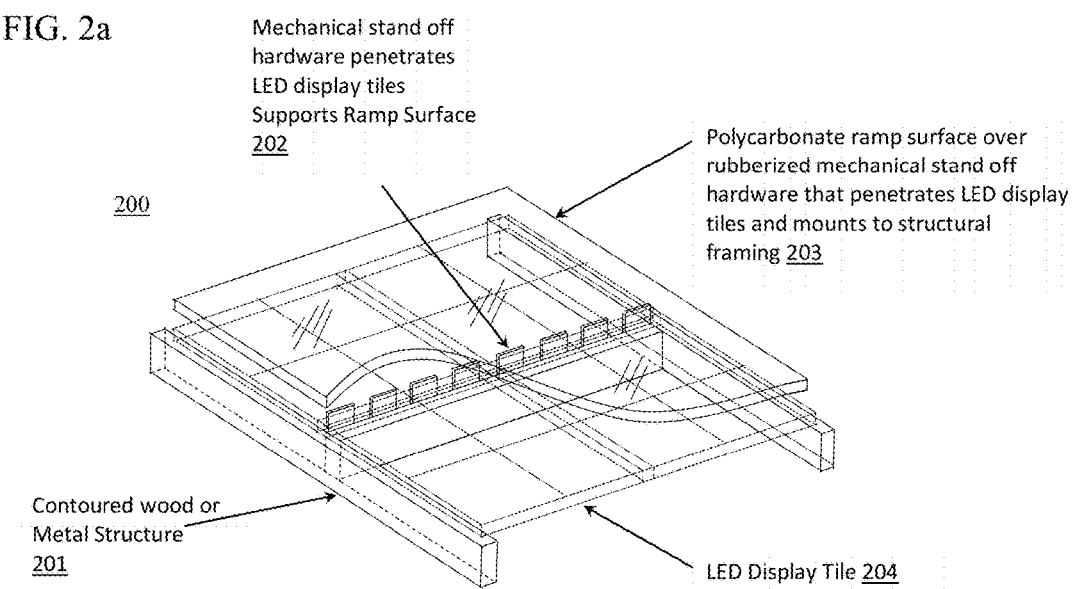
FIGS. 2a-2h illustrate a digital video ramp assembly, according to an embodiment.
Figure 2B:
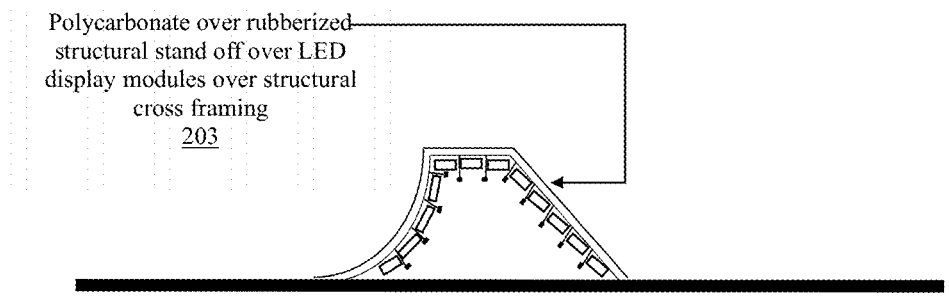
Figure 2C:
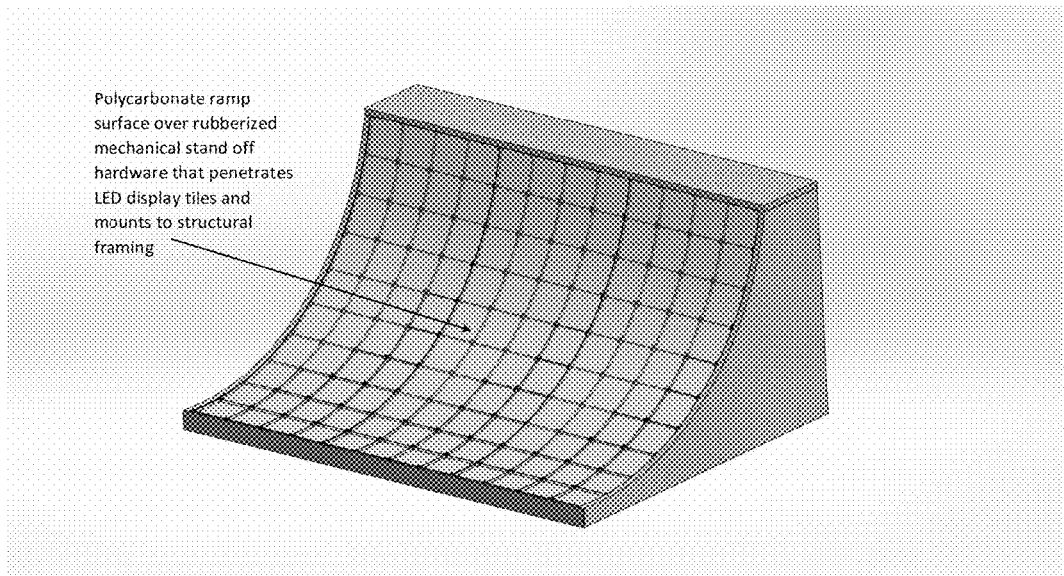
Figure 2D:
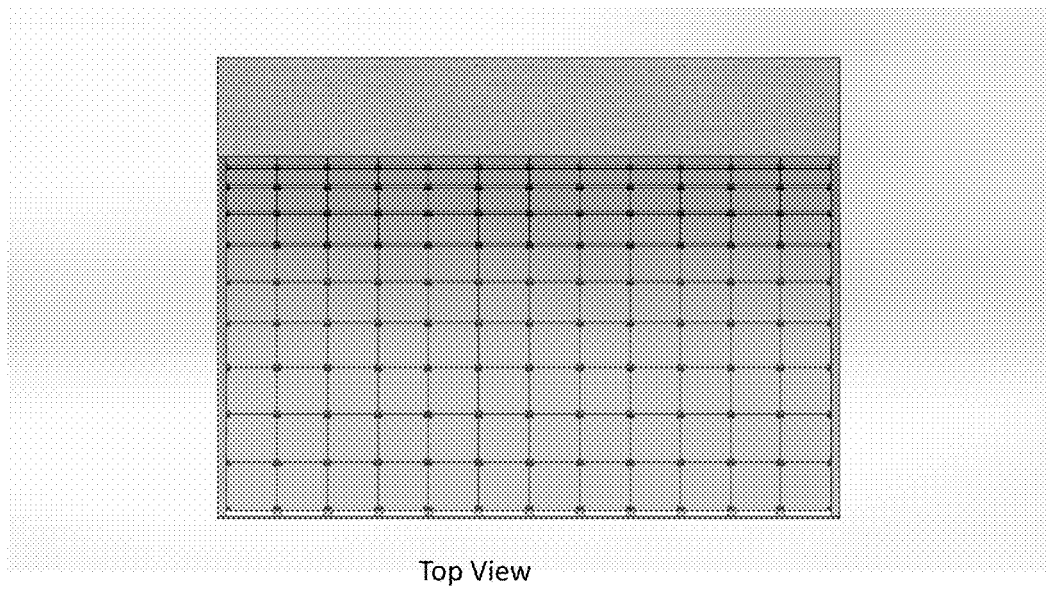
Figure 2E:
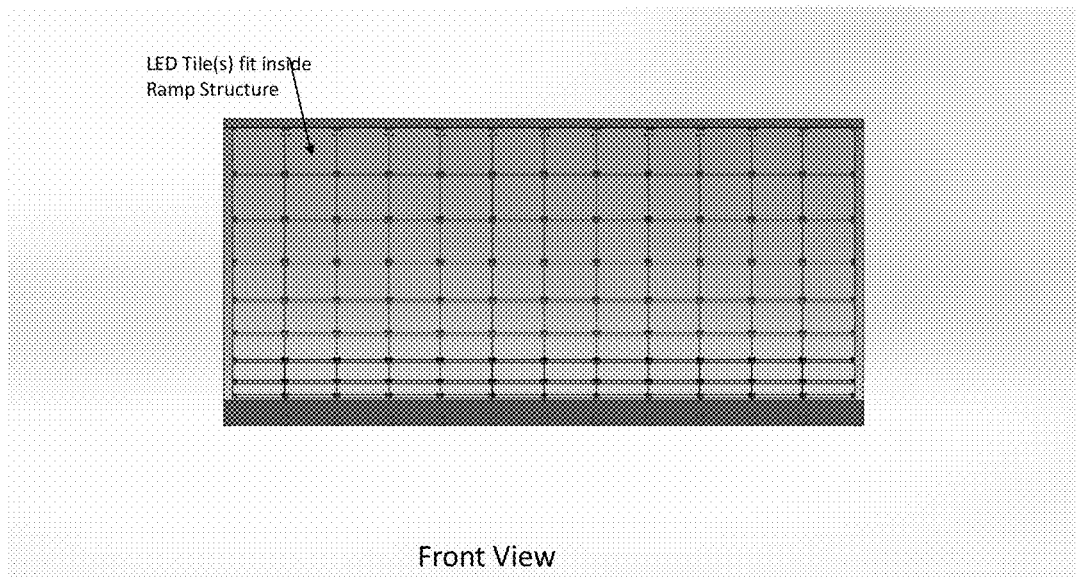
Figure 2F:
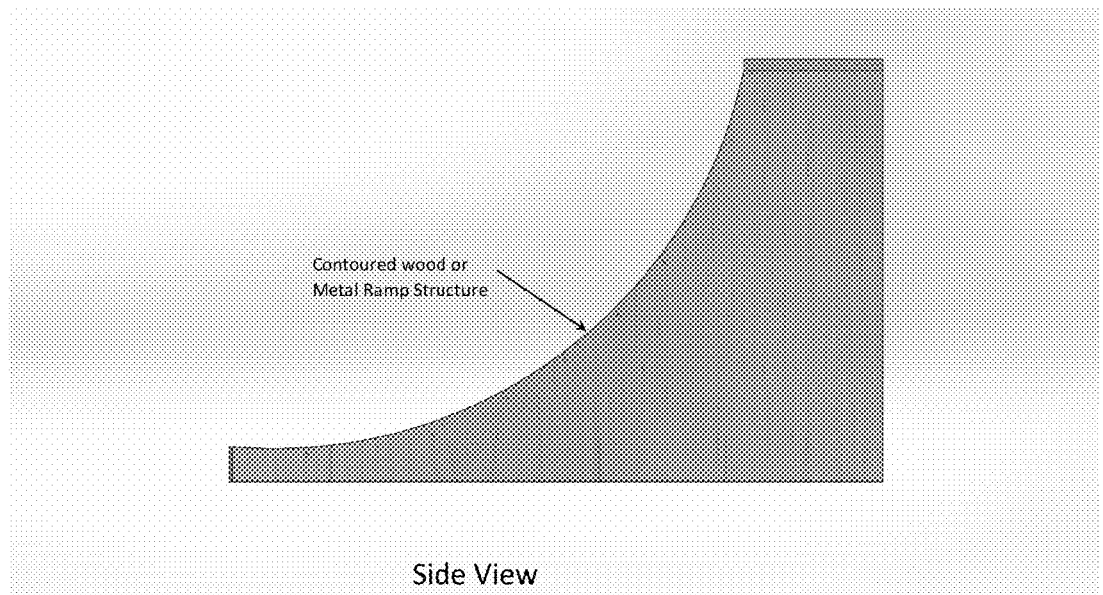
Figure 2G:
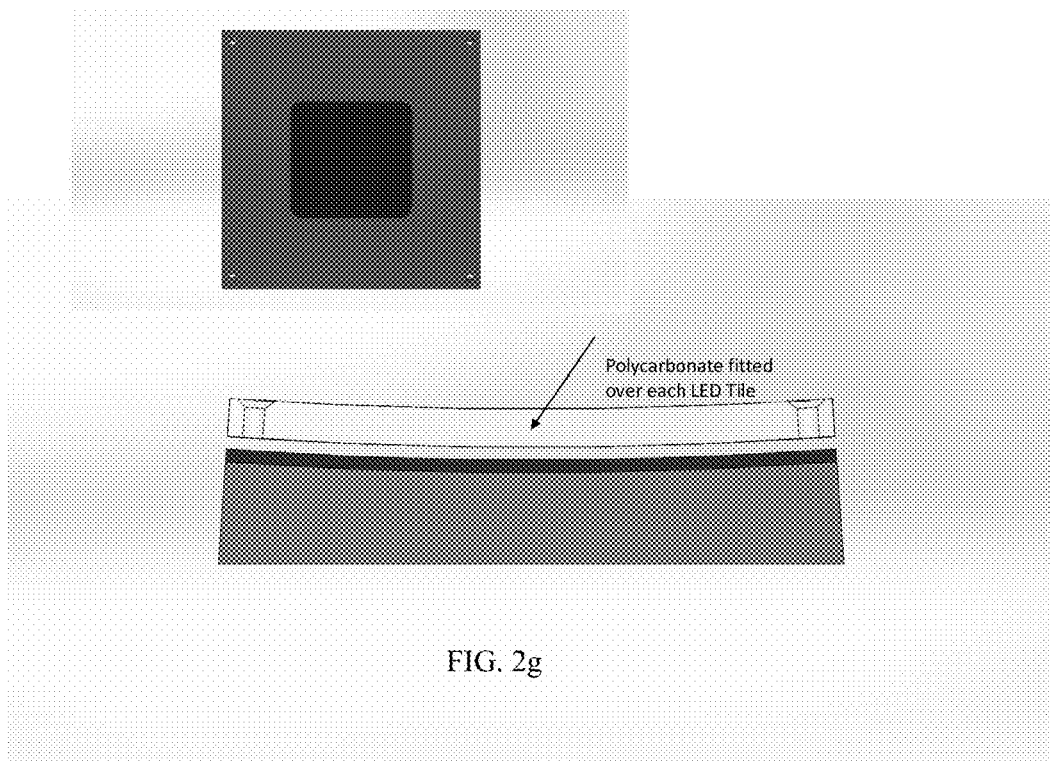
Figure 2H:
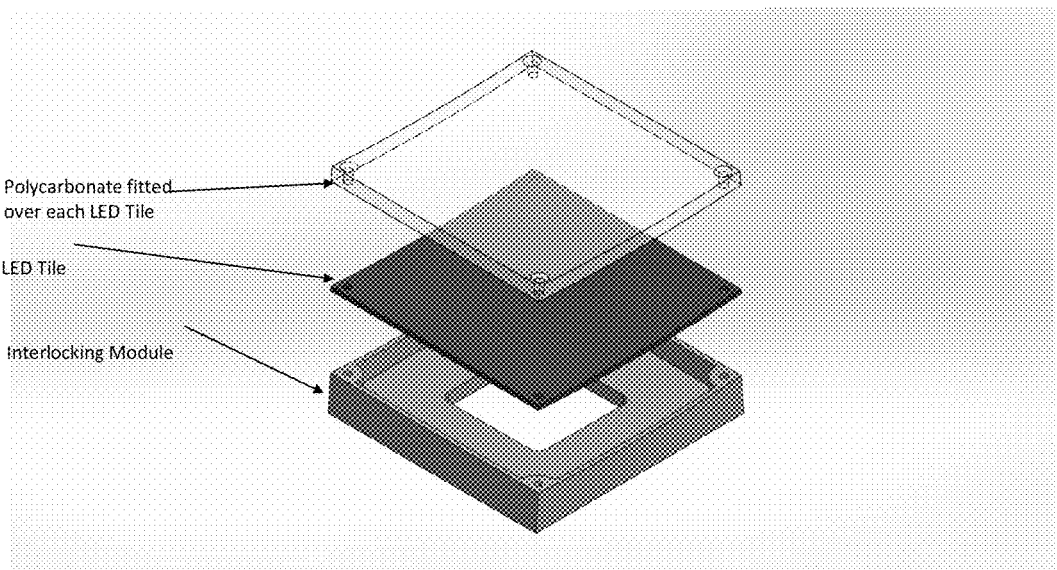

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein according to the following outline:

1.0. General Overview
2.0. Structural Overview
3.0. Motion Tracking
4.0. Signal Transmission and Control
5.0. Implementation Mechanism—Hardware Overview
6.0. Extensions and Alternatives

1.0. General Overview

Approaches, techniques, and mechanisms are disclosed for Digital Video Ramp. A method and computer apparatus are disclosed for a digital video ramp for skating, motocross, bicycle motocross (BMX) competitions and exhibition, entertainment, and advertising. The digital video ramp is a new ruggedized ramp system that will defy all senses of reality. Imagine a motorcyclist racing up the side of a ramp that looks like craggy old wood planks that spark and catch on fire. This is one of an infinite number of impossible ramp surface effects that the digital video ramp can create. The display mapped surfaces of the digital video ramp will act "chameleon like" in changing the skin of the ramp fixtures either as a standalone digital video ramp or several digital video ramps arranged and connected together in varying sizes and configurations. For some applications sections of the ramp may invert (face inward) such as barreled or coiled interior surfaces.

Advertising is another feature of the digital video ramp. Advertisements may be displayed on the surface of the digital video ramp during, for example, exhibitions or competitions. Typical ramp sizes are already large and well suited for advertising.

Gaming is yet another application of the digital video ramp. Players may ride along the digital video ramp and sensors placed in the vicinity of the ramp detect a player's position on the ramp and the display controller can change the scene being displayed around the player to reflect certain stages of the game.

The digital video ramp provides an alternative to conventional exhibition ramp structures in providing a dynamic, interactive video platform for exhibition, sporting events, entertainment, and advertising.

In an embodiment, the digital video ramp is a durable ramp assembly that utilizes clear ramp surface finishes with an LED video substrate. The clear ramp surfaces are the contact points for the skate boards, motorcycles, bicycles, etc., and provide an easily replaceable protective surface over the LED video substrate.

In an embodiment, a digital video ramp system includes a plurality of LED tiles, LED channels, LED embedded structural tile component and renewable enveloping layer of polycarbonate for ramp surfaces.

In other aspects, the invention encompasses computer apparatuses and computer-readable media configured to carry out the foregoing techniques.

Examples of related display systems are described in U.S. patent application Ser. No. 14/277,008, entitled "MODULAR MULTI-PANEL DIGITAL DISPLAY SYSTEM", filed on 13 May 2014, and which is hereby incorporated by reference in its entirety for all purposes.

2.0. Structural Overview

The construction of the digital video ramp may take the form of various scalable substructure assemblies. For example, FIGS. 1-4 illustrate four examples of digital video ramp assemblies that are modular and uniform.

Referring to FIG. 1, in an embodiment, an electronics package in conjunction with the digital video ramp 100 delivers video, sound, motion activation, lighting and interconnected features which will allow several ramps to be organized into an interactive video gaming environment.

In an embodiment, a polycarbonate ramp surface 104 is mounted over a uniform system of mechanical stand off hardware 102 which penetrates LED tiles 105 and is mounted to a structural ramp frame 107.

Referring also to FIGS. 2a-2h, the digital video ramp assembly 100 includes clear polycarbonate or other transparent suitable material surfaces (e.g., structural glass, acrylic, etc.) 104 overlaid onto structural LED linear channels of varying length which mount to varying form structural box framing. For example, a protective clear facing polycarbonate can be ⅜" Makrolon® polycarbonate, where a sheet is half the weight and 200 times stronger than glass.

In an embodiment, a digital video ramp assembly incorporates process-formed structural LED tiles with modular components that join in a system of scalable structural LED tiles forming a complete LED display structure with integrated LED embedded tiles with interlocking and inter-trans-positioning features sometimes requiring additional structural framing. LED tiles may be substituted with any type of display such as organic LED displays, high-performance backlight LCD displays, etc., that may be selected based on factors such as cost, application, power demands, etc.

In an embodiment, a digital video ramp assembly includes an integrated power supply, wiring channels, and digital image management software.

In an embodiment, a digital video ramp assembly includes a uniform polycarbonate ramp envelope which can be adapted to ramp systems as an additional layer of scratch and mar resistance with low cost renewable feature with lower cost predictive maintenance cycles.

The digital video ramp can be similar in stature to standard ramps, adhering to standard dimensions, radii, and slope. The digital video ramp structure is stable and can accommodate LED display systems with interlocking features and durable or protective clear ramp surface materials.

Figure 3A:
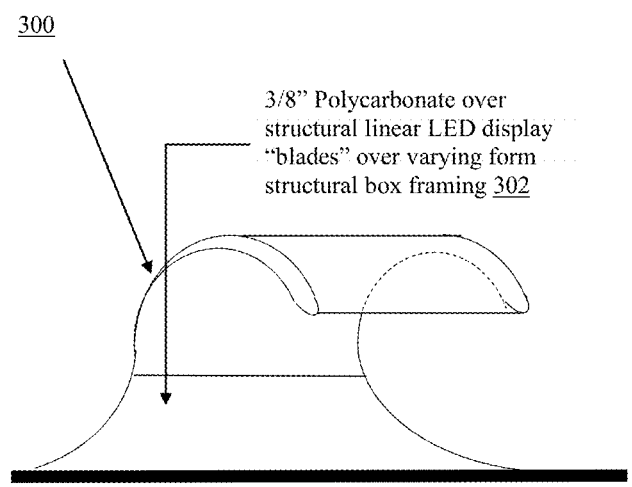
FIGS. 3a-3b illustrate a barreling wave digital video ramp assembly, according to an embodiment.
Figure 3B:
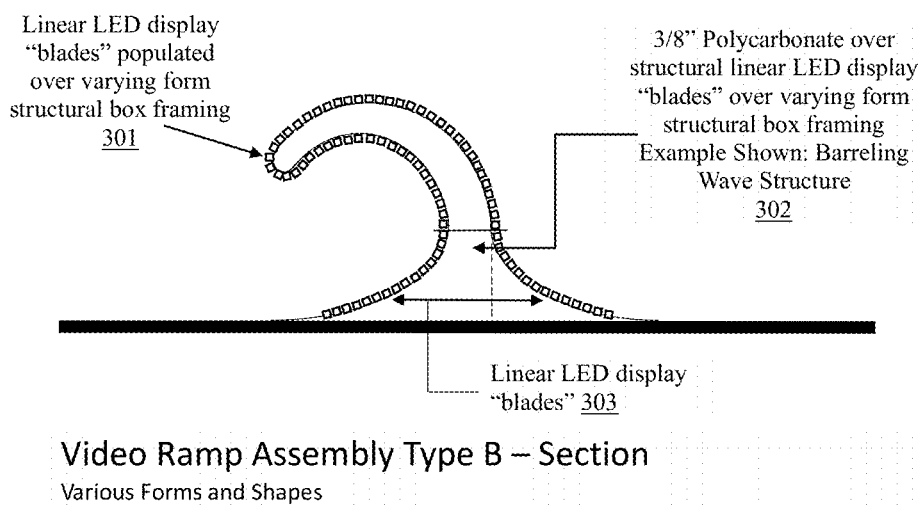

Referring to FIGS. 3a-3b, in an embodiment, a digital video ramp is comprised of polycarbonate over structural LED display channels ("blades") over varying form structural box framing 301. The ramp may take on any form such as a barreling wave structure 302.

Figure 4:
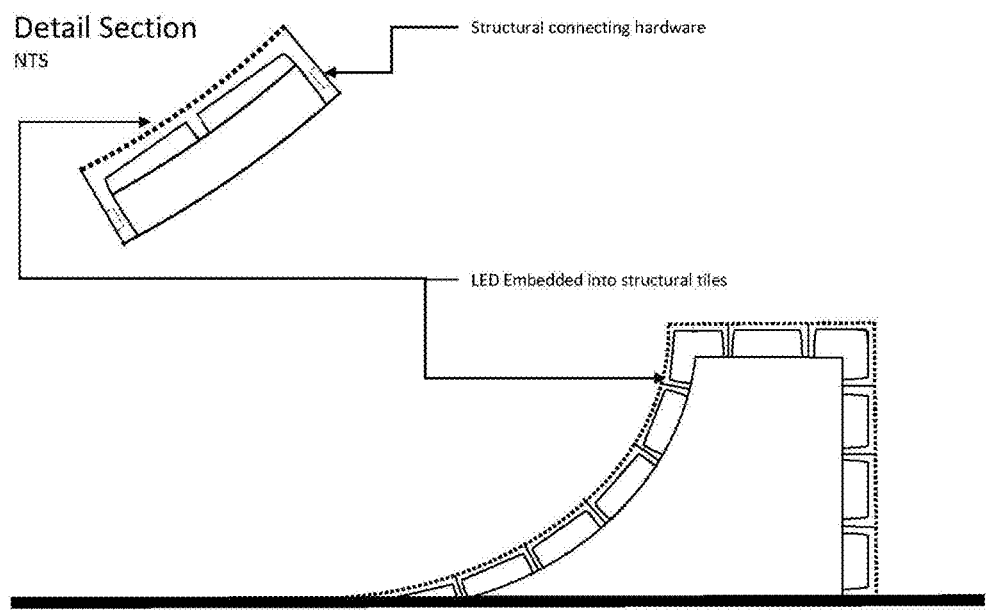
FIG. 4 illustrates a digital video ramp assembly with structural connecting LED embedded process formed tiles, according to an embodiment.
Figure 6A:
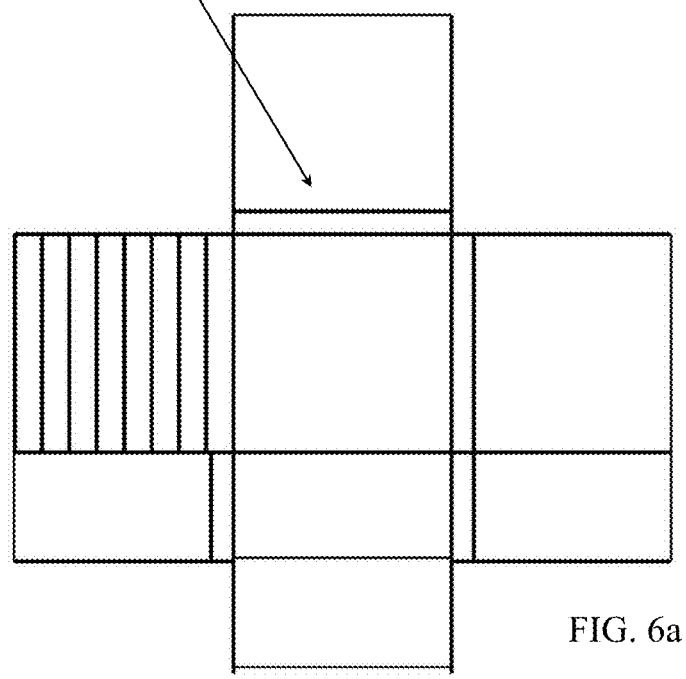
Figure 6B:
Figure 7A:
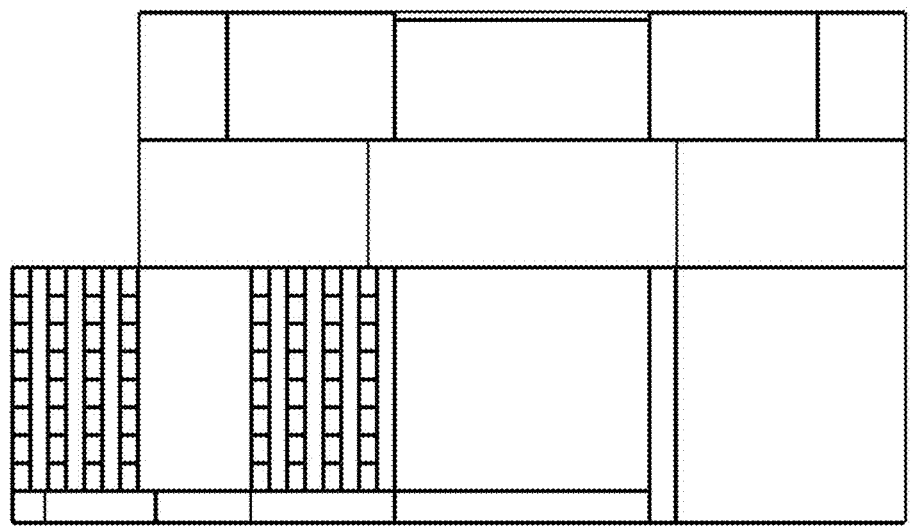
FIGS. 7a-7c illustrate a complex contour digital video ramp assembly, according to an embodiment.
Figure 7B:
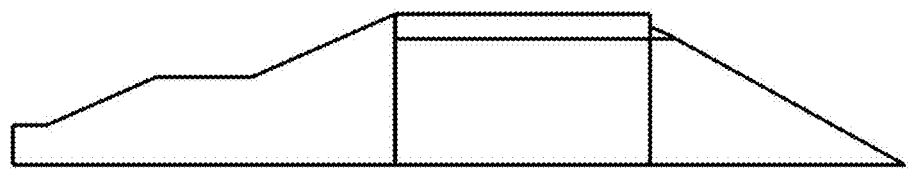
Figure 7C:
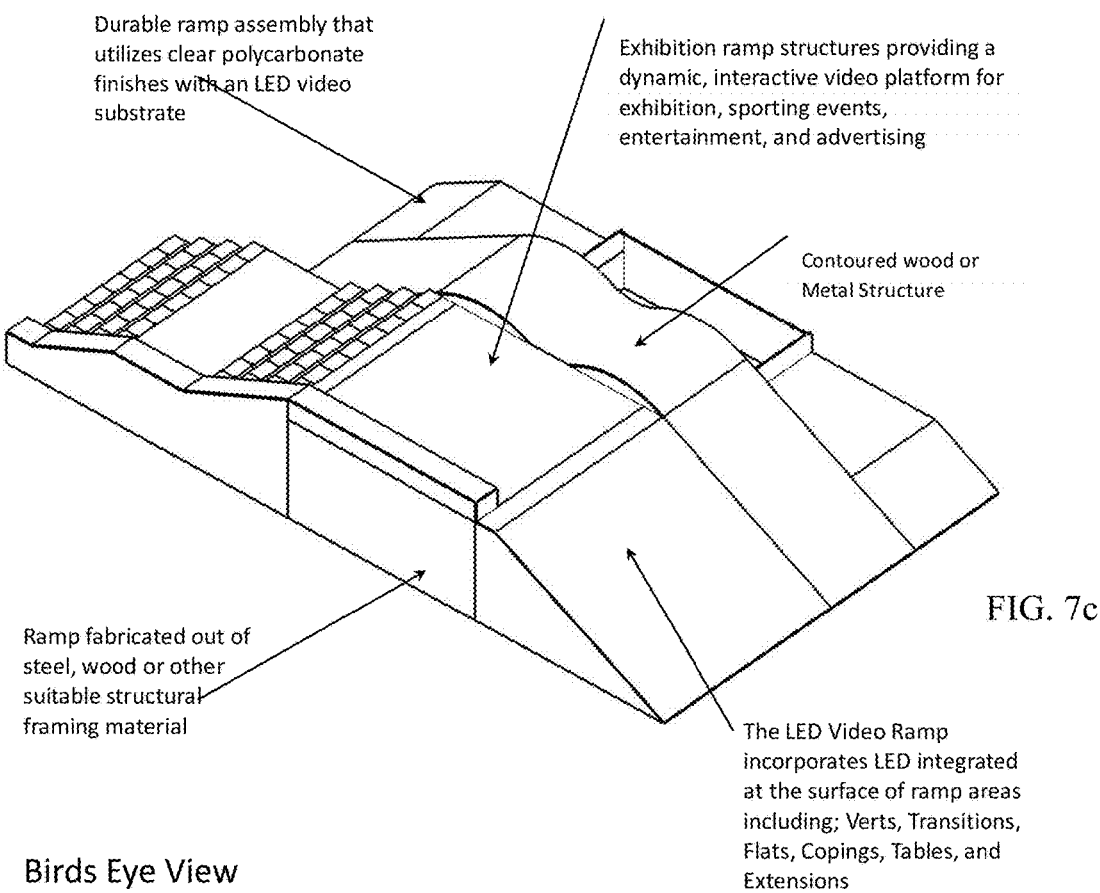

Referring to FIG. 4, in an embodiment, a digital video ramp may include structural, LED embedded process formed tiles.

Referring to FIG. 5, in an embodiment, a digital video ramp includes a formed polycarbonate layer shaped to fit over LED video ramp systems.

Referring to FIGS. 6a-6c and 7a-7c, embodiments include multi-surface ramp applications where there can be a large number of simple and complex contours on the ramp surfaces.

Each ramp assembly can incorporate integrated power supply wiring channels and digital image management software.

3.0. Motion Tracking

Figure 8:
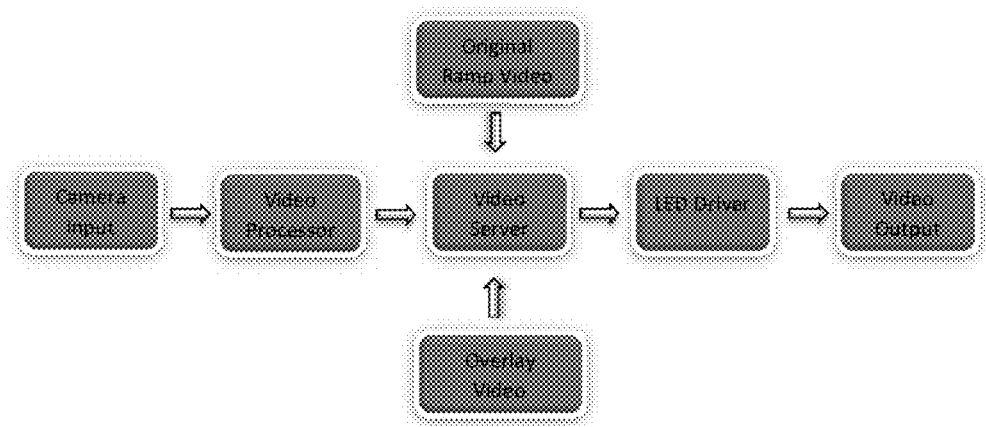
FIG. 8 illustrates a motion detection system for a digital video ramp assembly, according to an embodiment.

Referring to FIG. 8-9, in some embodiments, there are many methods of adaptable off the shelf interactive components suitable for operation of digital video ramps controlled by user interaction in video game play. Methods can include RFID x, y, and z coordinate; skateboard, bicycle, motorcycle path recognition, etc.

Some approaches may include:
1. Ultrasonic sensors: Linear array of narrow beam long throw ultrasonic sensors, alongside the ramp following the contour. These can sit up above the glass, but still be low enough to detect the skateboard wheel. Horizontal position on the ramp may be read by the strength of bounce back, vertical position tracked by what sensor is being hit. Resolution may be based on beam width. Testing for spacing can be important as bounce back from the wheels may ping other sensors.
2. Photo resistors: A matrix of photo resistors can be mounted under glass and above an LED display under the ramp surface. As light source is cut off from the diode it reports back to the video server. They can have a latency of approximately 10 milliseconds. Accuracy of the overlaid video stream can be based on the resolution of the matrix.
3. IMU Sensors: On board or body inertial measurement unit sensors. These sensors only record a relative position based on how far the sensor has moved since it was stationary. It can track how far it has moved in the X, Y and Z axis, but to track video over the display the skater would have to begin from the same origin point each time. This system may be useful for an instant replay, where the movements become translated into vectors to be displayed on screen.
4. Active RF or LE Bluetooth Transmitters/Receivers This can be useful for instore smartphone experiences.
5. IR Sensors: This would be good for indoor tracking There are many types of interactive components suitable for operation of digital video ramps controlled by user interaction in video game play. Methods would include RFID x, y, and z coordinate; skateboard, bicycle, motorcycle path recognition. Yet another method is motion sensing infra red technology. One embodiment using interactive motion tracking is reactive real time video described as follows:

The Digital Video Ramp interactive element is a reactive real time video feature that tracks the movement of a skater on the ramp to trigger overlaid video content on the ramp's surface display. As illustrated in the functional block diagram in FIGS. 8-9, cameras placed overhead can feed to a processor. The video processor can crop the video input to capture the ramp surface and detect the skater's movement and location (as seen in FIG. 9) by comparing the camera to the video being played on the ramp. When the video processor detects the movement captured by the camera the video processor can provide the location tracking coordinates to the video server, these coordinates can be updated, for example, at a minimum of 30 times per second. The server can play the overlay video, locating it based on the tracking location, and live compositing the entire video, main source and video overlay to the LED panels source equipment which feeds the LED drivers to play video to the LED display of the ramp's surface. The video will overlay on the existing playback and synchronize with the skater's movement in real time, tracking with the skater and following the orientation of the skater's movement vector. This additional layer of video will have the ability to be alpha-channel suppressed to allow for transparency in the overlay.

The control and tracking software may have minimal lag (less than 1/15th of a second) to allow the overlay video nearly instant response to the existence of a trackable object.

4.0. Signal Transmission and Control

Multi-line distribution of signal data comes from a central processing unit and supplied to an input signal of serial video and control data. Data is re-transmitted to LED digital video ramp display module(s) assembly. Similarly, data transmits the received serial video and control data signal to an input of data and to data input connector of LED digital video ramp display module(s) assembly. The data transmits the received serial video and control data to data input connector LED digital ramp display module(s) assembly. The data in signal is distributed to all LED digital ramp digital display module(s) assembly. The serial video and control data can be transferred from one LED module through ramp chassis assembly to the next LED digital display. In each case, the serial video and control data is re-transmitted by the control board of each LED digital display module.

A conventional power supply with an AC-to-DC converter and a voltage regulator to the LED digital video ramp display module is needed. Conventional DC cooling fans capable of providing a volume rate of airflow in order to maintain an operating temperature for LED digital ramp display module(s) can also be utilized. Insulation sheets for the power supply of a suitable material, such as mica may also be used.

The electrically connected elements of the LED digital ramp display control system may include: the RGB signal from the processing unit feeds a pre-processor; a pre-processor control bus output feeds a bank switch controller; a pre-processor control bus output feeds the CCD controller; a control bus output feeds bank switches that are connected to the row lines of the LED digital ramp display module(s); and a pulse width modulation control bus output feeds current sources that are connected to the column lines of the LED array via active switch devices, such as MOSFET switches or transistors; an analog voltage bus output of the LED digital ramp array feeds A/D converter; a digital voltage bus output converter feeds module interface; and a temperature data bus output feeds module interface. The LED digital video ramp display processing control bus output feeds module interface. Diagnostic information is available to processing unit via the data bus module.

In an embodiment, an apparatus comprises a processor and is configured to perform any of the foregoing methods.

In an embodiment, a non-transitory computer readable storage medium, storing software instructions, which when executed by one or more processors cause performance of any of the foregoing methods.

Note that, although separate embodiments are discussed herein, any combination of embodiments and/or partial embodiments discussed herein may be combined to form further embodiments.

5.0. Implementation Mechanism—Hardware Overview

According to one embodiment, the techniques described herein are implemented by one or more special-purpose computing devices. The special-purpose computing devices may be desktop computer systems, portable computer systems, handheld devices, smartphones, media devices, gaming consoles, networking devices, or any other device that incorporates hard-wired and/or program logic to implement the techniques. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques.

Figure 10:
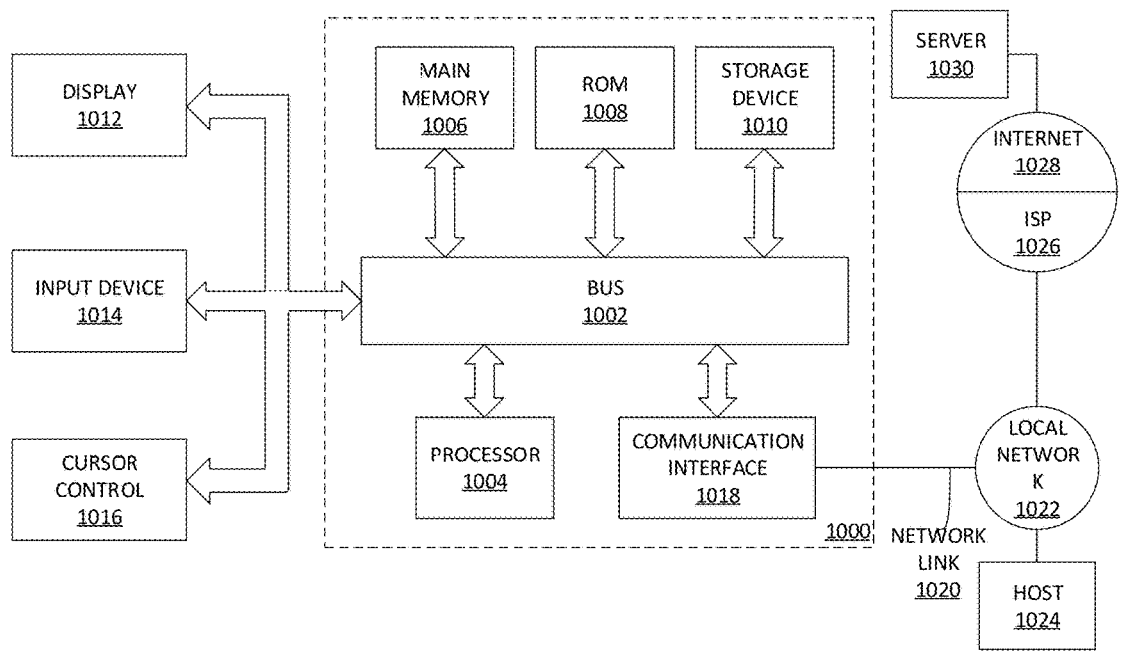
FIG. 10 is block diagram of a computer system upon which embodiments of the invention may be implemented.

FIG. 10 is a block diagram that illustrates a computer system 1000 utilized in implementing the above-described techniques, according to an embodiment. Computer system 1000 may be, for example, a desktop computing device, laptop computing device, tablet, smartphone, server appliance, computing mainframe, multimedia device, handheld device, networking apparatus, or any other suitable device.

Computer system 1000 includes one or more busses 1002 or other communication mechanism for communicating information, and one or more hardware processors 1004 coupled with busses 1002 for processing information. Hardware processors 1004 may be, for example, a general purpose microprocessor. Busses 1002 may include various internal and/or external components, including, without limitation, internal processor or memory busses, a Serial ATA bus, a PCI Express bus, a Universal Serial Bus, a HyperTransport bus, an Infiniband bus, and/or any other suitable wired or wireless communication channel.

Computer system 1000 also includes a main memory 1006, such as a random access memory (RAM) or other dynamic or volatile storage device, coupled to bus 1002 for storing information and instructions to be executed by processor 1004. Main memory 1006 also may be used for storing temporary variables or other intermediate information during execution of instructions to be executed by processor 1004. Such instructions, when stored in non-transitory storage media accessible to processor 1004, render computer system 1000 into a special-purpose machine that is customized to perform the operations specified in the instructions.

Computer system 1000 further includes one or more read only memories (ROM) 1008 or other static storage devices coupled to bus 1002 for storing static information and instructions for processor 1004. One or more storage devices 1010, such as a solid-state drive (SSD), magnetic disk, optical disk, or other suitable non-volatile storage device, is provided and coupled to bus 1002 for storing information and instructions.

Computer system 1000 may be coupled via bus 1002 to one or more displays 1012 for presenting information to a computer user. For instance, computer system 1000 may be connected via an High-Definition Multimedia Interface (HDMI) cable or other suitable cabling to a Liquid Crystal Display (LCD) monitor, and/or via a wireless connection such as peer-to-peer Wi-Fi Direct connection to a Light-Emitting Diode (LED) television. Other examples of suitable types of displays 1012 may include, without limitation, plasma display devices, projectors, cathode ray tube (CRT) monitors, electronic paper, virtual reality headsets, braille terminal, and/or any other suitable device for outputting information to a computer user. In an embodiment, any suitable type of output device, such as, for instance, an audio speaker or printer, may be utilized instead of a display 1012.

In an embodiment, output to display 1012 may be accelerated by one or more graphics processing unit (GPUs) in computer system 1000. A GPU may be, for example, a highly parallelized, multi-core floating point processing unit highly optimized to perform computing operations related to the display of graphics data, 3D data, and/or multimedia. In addition to computing image and/or video data directly for output to display 1012, a GPU may also be used to render imagery or other video data off-screen, and read that data back into a program for off-screen image processing with very high performance. Various other computing tasks may be off-loaded from the processor 1004 to the GPU.

One or more input devices 1014 are coupled to bus 1002 for communicating information and command selections to processor 1004. One example of an input device 1014 is a keyboard, including alphanumeric and other keys. Another type of user input device 1014 is cursor control 1016, such as a mouse, a trackball, or cursor direction keys for communicating direction information and command selections to processor 1004 and for controlling cursor movement on display 1012. This input device typically has two degrees of freedom in two axes, a first axis (e.g., x) and a second axis (e.g., y), that allows the device to specify positions in a plane. Yet other examples of suitable input devices 1014 include a touch-screen panel affixed to a display 1012, cameras, microphones, accelerometers, motion detectors, and/or other sensors. In an embodiment, a network-based input device 1014 may be utilized. In such an embodiment, user input and/or other information or commands may be relayed via routers and/or switches on a Local Area Network (LAN) or other suitable shared network, or via a peer-to-peer network, from the input device 1014 to a network link 1020 on the computer system 1000.

A computer system 1000 may implement techniques described herein using customized hard-wired logic, one or more ASICs or FPGAs, firmware and/or program logic which in combination with the computer system causes or programs computer system 1000 to be a special-purpose machine. According to one embodiment, the techniques herein are performed by computer system 1000 in response to processor 1004 executing one or more sequences of one or more instructions contained in main memory 1006. Such instructions may be read into main memory 1006 from another storage medium, such as storage device 1010. Execution of the sequences of instructions contained in main memory 1006 causes processor 1004 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical or magnetic disks, such as storage device 1010. Volatile media includes dynamic memory, such as main memory 1006. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 1002. Transmission media can also take the form of acoustic or light waves, such as those generated during radio-wave and infra-red data communications.

Various forms of media may be involved in carrying one or more sequences of one or more instructions to processor 1004 for execution. For example, the instructions may initially be carried on a magnetic disk or solid state drive of a remote computer. The remote computer can load the instructions into its dynamic memory and use a modem to send the instructions over a network, such as a cable network or cellular network, as modulated signals. A modem local to computer system 1000 can receive the data on the network and demodulate the signal to decode the transmitted instructions. Appropriate circuitry can then place the data on bus 1002. Bus 1002 carries the data to main memory 1006, from which processor 1004 retrieves and executes the instructions. The instructions received by main memory 1006 may optionally be stored on storage device 1010 either before or after execution by processor 1004.

A computer system 1000 may also include, in an embodiment, one or more communication interfaces 1018 coupled to bus 1002. A communication interface 1018 provides a data communication coupling, typically two-way, to a network link 1020 that is connected to a local network 1022. For example, a communication interface 1018 may be an integrated services digital network (ISDN) card, cable modem, satellite modem, or a modem to provide a data communication connection to a corresponding type of telephone line. As another example, the one or more communication interfaces 1018 may include a local area network (LAN) card to provide a data communication connection to a compatible LAN. As yet another example, the one or more communication interfaces 1018 may include a wireless network interface controller, such as a 802.11-based controller, Bluetooth controller, Long Term Evolution (LTE) modem, and/or other types of wireless interfaces. In any such implementation, communication interface 1018 sends and receives electrical, electromagnetic, or optical signals that carry digital data streams representing various types of information.

Network link 1020 typically provides data communication through one or more networks to other data devices. For example, network link 1020 may provide a connection through local network 1022 to a host computer 1024 or to data equipment operated by a Service Provider 1026. Service Provider 1026, which may for example be an Internet Service Provider (ISP), in turn provides data communication services through a wide area network, such as the world wide packet data communication network now commonly referred to as the "Internet" 1028. Local network 1022 and Internet 1028 both use electrical, electromagnetic or optical signals that carry digital data streams. The signals through the various networks and the signals on network link 1020 and through communication interface 1018, which carry the digital data to and from computer system 1000, are example forms of transmission media.

In an embodiment, computer system 1000 can send messages and receive data, including program code and/or other types of instructions, through the network(s), network link 1020, and communication interface 1018. In the Internet example, a server 1030 might transmit a requested code for an application program through Internet 1028, ISP 1026, local network 1022 and communication interface 1018. The received code may be executed by processor 1004 as it is received, and/or stored in storage device 1010, or other non-volatile storage for later execution. As another example, information received via a network link 1020 may be interpreted and/or processed by a software component of the computer system 1000, such as a web browser, application, or server, which in turn issues instructions based thereon to a processor 1004, possibly via an operating system and/or other intermediate layers of software components.

In an embodiment, some or all of the systems described herein may be or comprise server computer systems, including one or more computer systems 1000 that collectively implement various components of the system as a set of server-side processes. The server computer systems may include web server, application server, database server, and/or other conventional server components that certain above-described components utilize to provide the described functionality. The server computer systems may receive network-based communications comprising input data from any of a variety of sources, including without limitation user-operated client computing devices such as desktop computers, tablets, or smartphones, remote sensing devices, and/or other server computer systems.

In an embodiment, certain server components may be implemented in full or in part using "cloud"-based components that are coupled to the systems by one or more networks, such as the Internet. The cloud-based components may expose interfaces by which they provide processing, storage, software, and/or other resources to other components of the systems. In an embodiment, the cloud-based components may be implemented by third-party entities, on behalf of another entity for whom the components are deployed. In other embodiments, however, the described systems may be implemented entirely by computer systems owned and operated by a single entity.

In an embodiment, an apparatus comprises a processor and is configured to perform any of the foregoing methods. In an embodiment, a non-transitory computer readable storage medium, storing software instructions, which when executed by one or more processors cause performance of any of the foregoing methods.

6.0. Extensions and Alternatives

In the drawings, the various components are depicted as being communicatively coupled to various other components by arrows. These arrows illustrate only certain examples of information flows between the components. Neither the direction of the arrows nor the lack of arrow lines between certain components should be interpreted as indicating the existence or absence of communication between the certain components themselves. Indeed, each component may feature a suitable communication interface by which the component may become communicatively coupled to other components as needed to accomplish any of the functions described herein.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. In this regard, although specific claim dependencies are set out in the claims of this application, it is to be noted that the features of the dependent claims of this application may be combined as appropriate with the features of other dependent claims and with the features of the independent claims of this application, and not merely according to the specific dependencies recited in the set of claims. Moreover, although separate embodiments are discussed herein, any combination of embodiments and/or partial embodiments discussed herein may be combined to form further embodiments.

Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A digital video ramp comprising:
   a plurality of display tiles, each display tile configured to display video signals;
   a mechanical standoff structure having a plurality of rubberized standoffs, one or more rubberized standoffs of the plurality of rubberized standoffs penetrate each display tile of the plurality of display tiles inserted into the mechanical standoff structure;
   a transparent material surface overlaid onto the rubberized standoffs, over the plurality of display tiles, of the mechanical standoff structure;
   wherein the transparent material surface is contoured to match contours of the mechanical standoff structure;
   wherein the transparent material surface is configured to support one or more users traversing the transparent material surface;
   wherein the plurality of display tiles display video signals delivered from a video processing device.

2. The apparatus of claim 1, further comprising
   one or more sensors, the one or more sensors configured to detect movement across the transparent material surface;
   wherein the video processing device selects a video content to send to a set of display tiles among the plurality of display tiles based on a signal from the one or more sensors.

3. The apparatus of claim 2, wherein the one or more sensors include any combination of: ultrasonic sensors, photo resistors, inertial measurement unit sensors, active RF Transmitters/Receivers, LE Bluetooth Transmitters/Receivers, cameras, or IR sensors.

4. The apparatus of claim 1, further comprising
   one or more sensors, the one or more sensors configured to detect movement across the transparent material surface;
   wherein the one or more sensors include any combination of: ultrasonic sensors, photo resistors, inertial measurement unit sensors, active RF Transmitters/Receivers, LE Bluetooth Transmitters/Receivers, cameras, or IR sensors.

5. The apparatus of claim 1, wherein the plurality of display panels include any combination of: one or more organic LED displays or one or more high-performance backlight LCD displays.

6. The apparatus of claim 1, wherein the digital video ramp is a skate ramp.

7. The apparatus of claim 1, wherein the digital video ramp is a bicycle ramp.

8. The apparatus of claim 1, wherein the digital video ramp is a motorcycle ramp.

9. The apparatus of claim 1, further comprising
one or more sensors, the one or more sensors configured to detect movement across the transparent material surface;
wherein the video processing device tracks movement of a user and selects a video content to send to a set of display tiles among the plurality of display tiles based on a movement vector derived from one or more signals from the one or more sensors.

10. A method, comprising:
displaying display video signals over a plurality of display tiles, wherein the plurality of display tiles mounted to a mechanical standoff structure of a digital video ramp having a plurality of rubberized standoffs, wherein one or more rubberized standoffs of the plurality of rubberized standoffs penetrate each display tile of the plurality of display tiles inserted into the mechanical standoff structure;
wherein a transparent material surface is overlaid onto the rubberized standoffs, over the plurality of display tiles, of the mechanical standoff structure;
wherein the transparent material surface is contoured to match contours of the mechanical standoff structure;
wherein the transparent material surface is configured to support one or more users traversing the transparent material surface;
sending, by a video processing device, display video signals to the plurality of display tiles, wherein each display tile of the plurality of the display tiles display portions of the video signals.

11. The method of claim 10, further comprising
detecting movement across the transparent material surface using one or more sensors;
wherein the video processing device selects a video content to send to a set of display tiles among the plurality of display tiles based on a signal from the one or more sensors.

12. The method of claim 11, wherein the one or more sensors include any combination of: ultrasonic sensors, photo resistors, inertial measurement unit sensors, active RF Transmitters/Receivers, LE Bluetooth Transmitters/Receivers, cameras, or IR sensors.

13. The method of claim 10, further comprising
detecting movement across the transparent material surface using one or more sensors;
wherein the one or more sensors include any combination of: ultrasonic sensors, photo resistors, inertial measurement unit sensors, active RF Transmitters/Receivers, LE Bluetooth Transmitters/Receivers, cameras, or IR sensors.

14. The method of claim 10, wherein the plurality of display panels include any combination of: one or more organic LED displays or one or more high-performance backlight LCD displays.

15. The method of claim 10, wherein the digital video ramp is a skate ramp.

16. The method of claim 10, wherein the digital video ramp is a bicycle ramp.

17. The method of claim 10, wherein the digital video ramp is a motorcycle ramp.

18. The method of claim 10, further comprising
detecting movement across the transparent material surface using one or more sensors;
wherein the video processing device tracks movement of a user and selects a video content to send to a set of display tiles among the plurality of display tiles based on a movement vector derived from one or more signals from the one or more sensors.

* * * * *

UNITED STATES PATENT AND TRADEMARK OFFICE
CERTIFICATE OF CORRECTION

PATENT NO. : 9,943,745 B2
APPLICATION NO. : 15/003799
DATED : April 17, 2018
INVENTOR(S) : Steve Welck Page 1 of 1

It is certified that error appears in the above-identified patent and that said Letters Patent is hereby corrected as shown below:

On the Title Page

Item (73), Assignee: Delete "Weick" and insert --Welck--.

Signed and Sealed this
Twenty-fourth Day of July, 2018

Andrei Iancu
*Director of the United States Patent and Trademark Office*